United States Patent [19]

Fukuda et al.

[11] Patent Number: 5,536,659
[45] Date of Patent: Jul. 16, 1996

[54] DNA FRAGMENT COMPRISING A GENE ENCODING ETHYLENE FORMING ENZYME OF BACTERIA AND THE USE THEREOF

[75] Inventors: Hideo Fukuda, 5-10 Tezukayamanaka 3-chome, Sumiyosi-kug, Osaka-shi, Osaka 558; Takahira Ogawa, Kumamoto; Takao Fujii, Kumamoto; Kazuhiro Nagahama, Kumamoto, all of Japan

[73] Assignees: Hideo Fukuda; Iwatani Sangyo Kabushiki Kaisha (Itatani International Corporation), both of Osaka, Japan

[21] Appl. No.: 204,196

[22] PCT Filed: Sep. 14, 1993

[86] PCT No.: PCT/JP93/01309

§ 371 Date: Mar. 1, 1994

§ 102(e) Date: Mar. 1, 1994

[87] PCT Pub. No.: WO94/06914

PCT Pub. Date: Mar. 31, 1994

[30] Foreign Application Priority Data

Sep. 18, 1992 [JP] Japan ..................................... 4-275387

[51] Int. Cl.⁶ ............................. C12N 1/20; C12N 15/63; C07H 21/04
[52] U.S. Cl. .................................. 435/252.33; 435/320.1; 536/23.2
[58] Field of Search .................................. 435/252.3, 167, 435/252.33, 320.1; 536/23.2

[56] References Cited

U.S. PATENT DOCUMENTS 4,877,730 10/1989 Urushizaki et al. ..................... 435/132

OTHER PUBLICATIONS

Nagahama, K. et al. (1992) "Classification of ethylene—producing bacteria in terms of biosynthetic pathways to ethylene" *J. Ferment. Bioeng.* 73(1):1–5.

Fukuda et al., *Biochemical and Biophysical Research Communications, vol. 188, No. 2, Oct. 30, 1992, 826–832.*

Nagahama et al., *Journal of General Microbiology,* vol. 137, 1991, 2281–2286.

*Primary Examiner*—Robert A. Wax
*Assistant Examiner*—Kawai Lau
*Attorney, Agent, or Firm*—Bacon & Thomas

[57] ABSTRACT

Bacteria such as *E. coli* which are easy in manipulation are transformed by the gene encoding a ethylene-forming enzyme, and ethylene is formed by the transformants.

7 Claims, 2 Drawing Sheets

```
         10         20         30         40         50
GCGACCGCGTGTCAGCAACGACAATCCTTACTCGGAGTCGCTGTTCAGGACACTGAAGT 60         70         80         90        100        110
ACTGCCCGCAATGGCCGCAGGATGGGTTTGCCAGTCTTGACGCGGCACGCTCTGGGTGAG 120        130        140        150        160        170
GGATTTCATGCGTTGGTACAACAATGATCACCGGCACAGCCGAATCCGCTTCGTGACACC 180        190        200        210        220        230
GGCTGAGCGGCATCGAGGGCTGGATCATCAGATCCTGGCCAAGCGACATGAGCTGTACGA 240        250        260        270        280        290
GCTAGCCAGAGAGAAAAGGCCGGAGCGGTGGTCGAGGGAGACACGCAACTGGGAACCGAT 300        310        320        330        340        350
CGGCACCGTGCTGTTAAACCCGGATCGAGAGCAAGACGTTGAGAAAAAAGCAGCATAGTT 360        370        380        390        400        410
AGACGGTTGACGCGACAACTACCTTGAAAAACGCCGGCAGGGACGCTCATGATTCATGCT 420        430        440        450        460        470
CCAAGCAGGTGGGGTGTTTTTCCGTCGCTTGGACTTTGTTCTCCCGACGTCGTTTGGAAT 480        490        500        510        520        530
GAGCATCCGTCCCTTTATATGGATAAAGAAGAGACTAGCATGACCAACCTACAGACTTTC
                                          M  T  N  L  Q  T  F 540        550        560        570        580        590
GAGTTGCCTACCGAGGTAACCGGCTGCGCCGCCGATATCTCATTGGGAAGGGCGCTGATC
 E  L  P  T  E  V  T  G  C  A  A  D  I  S  L  G  R  A  L  I 600        610        620        630        640        650
CAAGCCTGGCAAAAAGATGGCATTTTTCAGATCAAGACCGATAGTGAGCAGGATCGCAAA
 Q  A  W  Q  K  D  G  I  F  Q  I  K  T  D  S  E  Q  D  R  K 660        670        680        690        700        710
ACGCAGGAAGCAATGGCTGCTAGCAAGCAGTTTTGCAAGGAACCGCTGACTTTTAAGAGT
 T  Q  E  A  M  A  A  S  K  Q  F  C  K  E  P  L  T  F  K  S 720        730        740        750        760        770
AGCTGCGTTAGCGATCTGACCTACAGCGGCTATGTTGCGTCAGGCGAGGAAGTCACAGCT
 S  C  V  S  D  L  T  Y  S  G  Y  V  A  S  G  E  E  V  T  A 780        790        800        810        820        830
GGTAAACCTGATTTCCCTGAAATCTTCACTGTCTGCAAGGACTTGTCGGTAGGCGATCAG
 G  K  P  D  F  P  E  I  F  T  V  C  K  D  L  S  V  G  D  Q 840        850        860        870        880        890
CGTGTAAAAGCCGGCTGGCCTTGCCATGGTCCGGTGCCATGGCCAAATAACACCTATCAG
 R  V  K  A  G  W  P  C  H  G  P  V  P  W  P  N  N  T  Y  Q 900        910        920        930        940        950
AAAAGCATGAAGACCTTCATGGAAGAGCTGGGTTTAGCGGGCGAACGGTTGCTCAAACTG
 K  S  M  K  T  F  M  E  E  L  G  L  A  G  E  R  L  L  K  L
```

FIG. 1

```
      960       970       980       990       1000      1010
ACAGCGCTCGGCTTTGAACTACCCATCAACACGTTCACCGACTTAACTCGCGATGGTTGG
 T  A  L  G  F  E  L  P  I  N  T  F  T  D  L  T  R  D  G  W 1020      1030      1040      1050      1060      1070
CACCACATGCGTGTATTACGCTTCCCGCCCCAAACATCCACGCTGTCCCGTGGAATTGGT
 H  H  M  R  V  L  R  F  P  P  Q  T  S  T  L  S  R  G  I  G 1080      1090      1100      1110      1120      1130
GCGCACACTGACTATGGGTTGTTGGTAATTGCCGCTCAGGACGATGTTGGTGGCTTATAT
 A  H  T  D  Y  G  L  L  V  I  A  A  Q  D  D  V  G  G  L  Y 1140      1150      1160      1170      1180      1190
ATTCGCCCTCCAGTCGAGGGAGAGAAGCGTAATCGTAACTGGTTGCCTGGTGAGAGCTCA
 I  R  P  P  V  E  G  E  K  R  N  R  N  W  L  P  G  E  S  S 1200      1210      1220      1230      1240      1250
GCAGGCATGTTTGAGCACGATGAACCTTGGACCTTCGTGACGCCCACCCCAGGCGTGTGG
 A  G  M  F  E  H  D  E  P  W  T  F  V  T  P  T  P  G  V  W 1260      1274      1280      1290      1300      1310
ACAGTTTTCCCAGGTGATATCTTGCAGTTCATGACCGGCGGCCAGCTGCTTTCCACTCCG
 T  V  F  P  G  D  I  L  Q  F  M  T  G  G  Q  L  L  S  T  P 1320      1330      1340      1350      1360      1370
CACAAGGTTAAGCTCAATACCCGCGAACGTTTCGCCTGCGCTTATTTTCATGAGCCTAAT
 H  K  V  K  L  N  T  R  E  R  F  A  C  A  Y  F  H  E  P  N 1380      1390      1400      1410      1420      1430
TTTGAAGCATCCGCCTATCCGTTGTTCGAGCCCAGCGCCAATGAGCGTATTCATTATGGT
 F  E  A  S  A  Y  P  L  F  E  P  S  A  N  E  R  I  H  Y  G 1440      1450      1460      1470      1480      1490
GAGCACTTTACCAACATGTTTATGCGTTGCTATCCAGATCGGATCACCACCCAGAGGATC
 E  H  F  T  N  M  F  M  R  C  Y  P  D  R  I  T  T  Q  R  I 1500      1510      1520      1530      1540      1550
AACAAGGAGAATCGCCTGGCGCACTTGGAGGACTTGAAGAAGTATTCGGACACCCGCGCG
 N  K  E  N  R  L  A  H  L  E  D  L  K  K  Y  S  D  T  R  A 1560      1570      1580      1598      1600      1610
ACAGGCTCATGAGTCGACACCCTGCCCGGTGCTGCCGGACAGGGGCCTTATCGTTACTGG
 T  G  S 1620      1630      1640      1650      1660      1670
TGACTAATAATTGGCATATCAATGTCCACTCAGCACCCAGATCTTATGATCTGGGTGCTG 1680      1690      1700      1710      1720      1730
AGTGGAGCAATGTAACCATTATGCTGAGCGTTCATGCATAGGAATTTCAATAATTCCTAT 1740      1750      1760      1770      1780      1790
ACAAGGCAATCCGCCGAAAAAGGTCCCCTCGGCGTGATGCCAACGTGGCGTCGATGTCGG

1800
CAAAAAGCTT
```

FIG. 2

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 350 amino acids
        ( B ) TYPE: amino acid
        ( C ) STRANDEDNESS: double
        ( D ) TOPOLOGY: circular ( i i ) MOLECULE TYPE: DNA (genomic)

( x i ) SEQUENCE DESCRIPTION: SEQ ID NO:1:

Met Thr Asn Leu Gln Thr Phe Glu Leu Pro Thr Glu Val Thr Gly Cys

|   |   |   |   | 1 |   |   |   |   | 5 |   |   |   |   | 10 |   |   |   |   | 15 |
|---|---|---|---|---|---|---|---|---|---|---|---|---|---|---|---|---|---|---|---|
| Ala | Ala | Asp | Ile<br>20 | Ser | Leu | Gly | Arg | Ala | Leu<br>25 | Ile | Gln | Ala | Trp<br>30 | Gln | Lys |
| Asp | Gly | Ile<br>35 | Phe | Gln | Ile | Lys | Thr<br>40 | Asp | Ser | Glu | Gln | Asp<br>45 | Arg | Lys | Thr |
| Gln | Glu<br>50 | Ala | Met | Ala | Ala | Ser<br>55 | Lys | Gln | Phe | Cys | Lys<br>60 | Glu | Pro | Leu | Thr |
| Phe<br>65 | Lys | Ser | Ser | Cys | Val<br>70 | Ser | Asp | Leu | Thr | Tyr<br>75 | Ser | Gly | Tyr | Val | Ala<br>80 |
| Ser | Gly | Glu | Glu | Val<br>85 | Thr | Ala | Gly | Lys | Pro<br>90 | Asp | Phe | Pro | Glu | Ile<br>95 | Phe |
| Thr | Val | Cys | Lys<br>100 | Asp | Leu | Ser | Val | Gly<br>105 | Asp | Gln | Arg | Val | Lys<br>110 | Ala | Gly |
| Trp | Pro | Cys<br>115 | His | Gly | Pro | Val | Pro<br>120 | Trp | Pro | Asn | Asn | Thr<br>125 | Tyr | Gln | Lys |
| Ser | Met<br>130 | Lys | Thr | Phe | Met | Glu<br>135 | Glu | Leu | Gly | Leu | Ala<br>140 | Gly | Glu | Arg | Leu |
| Leu<br>145 | Lys | Leu | Thr | Ala | Leu<br>150 | Gly | Phe | Glu | Leu | Pro<br>155 | Ile | Asn | Thr | Phe | Thr<br>160 |
| Asp | Leu | Thr | Arg | Asp<br>165 | Gly | Trp | His | His | Met<br>170 | Arg | Val | Leu | Arg | Phe<br>175 | Pro |
| Pro | Gln | Thr | Ser<br>180 | Thr | Leu | Ser | Arg | Gly<br>185 | Ile | Gly | Ala | His | Thr<br>190 | Asp | Tyr |
| Gly | Leu | Leu<br>195 | Val | Ile | Ala | Ala | Gln<br>200 | Asp | Asp | Val | Gly | Gly<br>205 | Leu | Tyr | Ile |
| Arg | Pro<br>210 | Pro | Val | Glu | Gly | Glu<br>215 | Lys | Arg | Asn | Arg | Asn<br>220 | Trp | Leu | Pro | Gly |
| Glu<br>225 | Ser | Ser | Ala | Gly | Met<br>230 | Phe | Glu | His | Asp | Glu<br>235 | Pro | Trp | Thr | Phe | Val<br>240 |
| Thr | Pro | Thr | Pro | Gly<br>245 | Val | Trp | Thr | Val | Phe<br>250 | Pro | Gly | Asp | Ile | Leu<br>255 | Gln |
| Phe | Met | Thr | Gly<br>260 | Gly | Gln | Leu | Leu | Ser<br>265 | Thr | Pro | His | Lys | Val<br>270 | Lys | Leu |
| Asn | Thr | Arg<br>275 | Glu | Arg | Phe | Ala | Cys<br>280 | Ala | Tyr | Phe | His | Glu<br>285 | Pro | Asn | Phe |
| Glu | Ala<br>290 | Ser | Ala | Tyr | Pro | Leu<br>295 | Phe | Glu | Pro | Ser | Ala<br>300 | Asn | Glu | Arg | Ile |
| His<br>305 | Tyr | Gly | Glu | His | Phe<br>310 | Thr | Asn | Met | Phe | Met<br>315 | Arg | Cys | Tyr | Pro | Asp<br>320 |
| Arg | Ile | Thr | Thr | Gln<br>325 | Arg | Ile | Asn | Lys | Glu<br>330 | Asn | Arg | Leu | Ala | His<br>335 | Leu |
| Glu | Asp | Leu | Lys<br>340 | Lys | Tyr | Ser | Asp | Thr<br>345 | Arg | Ala | Thr | Gly | Ser<br>350 |   |   |

(2) INFORMATION FOR SEQ ID NO:2:

(i) SEQUENCE CHARACTERISTICS:
        (A) LENGTH: 1050 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:2:

```
ATGACCAACC TACAGACTTT CGAGTTGCCT ACCGAGGTAA CCGGCTGCGC CGCCGATATC    60
```

| | | | | | |
|---|---|---|---|---|---|
| TCATTGGGAA | GGGCGCTGAT | CCAAGCCTGG | CAAAAAGATG | GCATTTTTCA | GATCAAGACC | 120 |
| GATAGTGAGC | AGGATCGCAA | AACGCAGGAA | GCAATGGCTG | CTAGCAAGCA | GTTTTGCAAG | 180 |
| GAACCGCTGA | CTTTTAAGAG | TAGCTGCGTT | AGCGATCTGA | CCTACAGCGG | CTATGTTGCG | 240 |
| TCAGGCGAGG | AAGTCACAGC | TGGTAAACCT | GATTTCCCTG | AAATCTTCAC | TGTCTGCAAG | 300 |
| GACTTGTCGG | TAGGCGATCA | GCGTGTAAAA | GCCGGCTGGC | CTTGCCATGG | TCCGGTGCCA | 360 |
| TGGCCAAATA | ACACCTATCA | GAAAAGCATG | AAGACCTTCA | TGGAAGAGCT | GGGTTTAGCG | 420 |
| GGCGAACGGT | TGCTCAAACT | GACAGCGCTC | GGCTTTGAAC | TACCCATCAA | CACGTTCACC | 480 |
| GACTTAACTC | GCGATGGTTG | GCACCACATG | CGTGTATTAC | GCTTCCCGCC | CCAAACATCC | 540 |
| ACGCTGTCCC | GTGGAATTGG | TGCGCACACT | GACTATGGGT | TGTTGGTAAT | TGCCGCTCAG | 600 |
| GACGATGTTG | GTGGCTTATA | TATTCGCCCT | CCAGTCGAGG | GAGAGAAGCG | TAATCGTAAC | 660 |
| TGGTTGCCTG | GTGAGAGCTC | AGCAGGCATG | TTTGAGCACG | ATGAACCTTG | GACCTTCGTG | 720 |
| ACGCCCACCC | CAGGCGTGTG | GACAGTTTTC | CCAGGTGATA | TCTTGCAGTT | CATGACCGGC | 780 |
| GGCCAGCTGC | TTTCCACTCC | GCACAAGGTT | AAGCTCAATA | CCCGCGAACG | TTTCGCCTGC | 840 |
| GCTTATTTTC | ATGAGCCTAA | TTTTGAAGCA | TCCGCCTATC | CGTTGTTCGA | GCCCAGCGCC | 900 |
| AATGAGCGTA | TTCATTATGG | TGAGCACTTT | ACCAACATGT | TTATGCGTTG | CTATCCAGAT | 960 |
| CGGATCACCA | CCCAGAGGAT | CAACAAGGAG | AATCGCCTGG | CGCACTTGGA | GGACTTGAAG | 1020 |
| AAGTATTCGG | ACACCCGCGC | GACAGGCTCA | | | | 1050 |

(2) INFORMATION FOR SEQ ID NO:3:

(i) SEQUENCE CHARACTERISTICS:
        (A) LENGTH: 1809 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:3:

| | | | | | |
|---|---|---|---|---|---|
| GCGACCGCGT | GTCAGCAACG | ACAATCCTTA | CTCGGAGTCG | CTGTTCAGGA | CACTGAAGTA | 60 |
| CTGCCCGCAA | TGGCCGCAGG | ATGGGTTTGC | CAGTCTTGAC | GCGGCACGCT | CTGGGTGAGG | 120 |
| GATTTCATGC | GTTGGTACAA | CAATGATCAC | CGGCACAGCC | GAATCCGCTT | CGTGACACCG | 180 |
| GCTGAGCGGC | ATCGAGGGCT | GGATCATCAG | ATCCTGGCCA | AGCGACATGA | GCTGTACGAG | 240 |
| CTAGCCAGAG | AGAAAAGGCC | GGAGCGGTGG | TCGAGGGAGA | CACGCAACTG | GGAACCGATC | 300 |
| GGCACCGTGC | TGTTAAACCC | GGATCGAGAG | CAAGACGTTG | AGAAAAAGC | AGCATAGTTA | 360 |
| GACGGTTGAC | GCGACAACTA | CCTTGAAAAA | CGCCGGCAGG | GACGCTCATG | ATTCATGCTC | 420 |
| CAAGCAGGTG | GGGTGTTTTT | CCGTCGCTTG | GACTTTGTTC | TCCCGACGTC | GTTTGGAATG | 480 |
| AGCATCCGTC | CCTTTATATG | GATAAAGAAG | AGACTAGCAT | GACCAACCTA | CAGACTTTCG | 540 |
| AGTTGCCTAC | CGAGGTAACC | GGCTGCGCCG | CCGATATCTC | ATTGGGAAGG | GCGCTGATCC | 600 |
| AAGCCTGGCA | AAAAGATGGC | ATTTTTCAGA | TCAAGACCGA | TAGTGAGCAG | GATCGCAAAA | 660 |
| CGCAGGAAGC | AATGGCTGCT | AGCAAGCAGT | TTTGCAAGGA | ACCGCTGACT | TTTAAGAGTA | 720 |
| GCTGCGTTAG | CGATCTGACC | TACAGCGGCT | ATGTTGCGTC | AGGCGAGGAA | GTCACAGCTG | 780 |
| GTAAACCTGA | TTTCCCTGAA | ATCTTCACTG | TCTGCAAGGA | CTTGTCGGTA | GGCGATCAGC | 840 |
| GTGTAAAAGC | CGGCTGGCCT | TGCCATGGTC | CGGTGCCATG | GCCAAATAAC | ACCTATCAGA | 900 |
| AAAGCATGAA | GACCTTCATG | GAAGAGCTGG | GTTTAGCGGG | CGAACGGTTG | CTCAAACTGA | 960 |
| CAGCGCTCGG | CTTTGAACTA | CCCATCAACA | CGTTCACCGA | CTTAACTCGC | GATGGTTGGC | 1020 |

```
ACCACATGCG TGTATTACGC TTCCCGCCCC AAACATCCAC GCTGTCCCGT GGAATTGGTG        1080

CGCACACTGA CTATGGGTTG TTGGTAATTG CCGCTCAGGA CGATGTTGGT GGCTTATATA        1140

TTCGCCCTCC AGTCGAGGGA GAGAAGCGTA ATCGTAACTG GTTGCCTGGT GAGAGCTCAG        1200

CAGGCATGTT TGAGCACGAT GAACCTTGGA CCTTCGTGAC GCCCACCCCA GGCGTGTGGA        1260

CAGTTTTCCC AGGTGATATC TTGCAGTTCA TGACCGGCGG CCAGCTGCTT TCCACTCCGC        1320

ACAAGGTTAA GCTCAATACC CGCGAACGTT TCGCCTGCGC TTATTTTCAT GAGCCTAATT        1380

TTGAAGCATC CGCCTATCCG TTGTTCGAGC CCAGCGCCAA TGAGCGTATT CATTATGGTG        1440

AGCACTTTAC CAACATGTTT ATGCGTTGCT ATCCAGATCG GATCACCACC CAGAGGATCA        1500

ACAAGGAGAA TCGCCTGGCG CACTTGGAGG ACTTGAAGAA GTATTCGGAC ACCCGCGCGA        1560

CAGGCTCATG AGTCGACACC CTGCCCGGTG CTGCCGGACA GGGGCCTTAT CGTTACTGGT        1620

GACTAATAAT TGGCATATCA ATGTCCACTC AGCACCCAGA TCTTATGATC TGGGTGCTGA        1680

GTGGAGCAAT GTAACCATTA TGCTGAGCGT TCATGCATAG GAATTCAAT AATTCCTATA        1740

CAAGGCAATC CGCCGAAAAA GGTCCCCTCG GCGTGATGCC AACGTGGCGT CGATGTCGGC        1800

AAAAAGCTT                                                                 1809
```

( 2 ) INFORMATION FOR SEQ ID NO:4:

( i ) SEQUENCE CHARACTERISTICS:
        ( A ) LENGTH: 1809 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 519..1568

( x i ) SEQUENCE DESCRIPTION: SEQ ID NO:4:

```
GCGACCGCGT GTCAGCAACG ACAATCCTTA CTCGGAGTCG CTGTTCAGGA CACTGAAGTA        60

CTGCCCGCAA TGGCCGCAGG ATGGGTTTGC CAGTCTTGAC GCGGCACGCT CTGGGTGAGG       120

GATTTCATGC GTTGGTACAA CAATGATCAC CGGCACAGCC GAATCCGCTT CGTGACACCG       180

GCTGAGCGGC ATCGAGGGCT GGATCATCAG ATCCTGGCCA AGCGACATGA GCTGTACGAG       240

CTAGCCAGAG AGAAAAGGCC GGAGCGGTGG TCGAGGGAGA CACGCAACTG GAACCGATC        300

GGCACCGTGC TGTTAAACCC GGATCGAGAG CAAGACGTTG AGAAAAAAGC AGCATAGTTA       360

GACGGTTGAC GCGACAACTA CCTTGAAAAA CGCCGGCAGG GACGCTCATG ATTCATGCTC       420

CAAGCAGGTG GGGTGTTTTT CCGTCGCTTG GACTTTGTTC TCCCGACGTC GTTTGGAATG       480

AGCATCCGTC CCTTTATATG GATAAGAAG AGACTAGC ATG ACC AAC CTA CAG            533
                                            Met Thr Asn Leu Gln
                                             1                5

ACT TTC GAG TTG CCT ACC GAG GTA ACC GGC TGC GCC GCC GAT ATC TCA         581
Thr Phe Glu Leu Pro Thr Glu Val Thr Gly Cys Ala Ala Asp Ile Ser
             10                  15                  20

TTG GGA AGG GCG CTG ATC CAA GCC TGG CAA AAA GAT GGC ATT TTT CAG         629
Leu Gly Arg Ala Leu Ile Gln Ala Trp Gln Lys Asp Gly Ile Phe Gln
         25                  30                  35

ATC AAG ACC GAT AGT GAG CAG GAT CGC AAA ACG CAG GAA GCA ATG GCT         677
Ile Lys Thr Asp Ser Glu Gln Asp Arg Lys Thr Gln Glu Ala Met Ala
         40                  45                  50

GCT AGC AAG CAG TTT TGC AAG GAA CCG CTG ACT TTT AAG AGT AGC TGC         725
Ala Ser Lys Gln Phe Cys Lys Glu Pro Leu Thr Phe Lys Ser Ser Cys
```

-continued

| | | | | | | | | | | | | | | | | |
|---|---|---|---|---|---|---|---|---|---|---|---|---|---|---|---|---|
| | | 55 | | | | | 60 | | | | | 65 | | | | |
| GTT | AGC | GAT | CTG | ACC | TAC | AGC | GGC | TAT | GTT | GCG | TCA | GGC | GAG | GAA | GTC | 773 |
| Val | Ser | Asp | Leu | Thr | Tyr | Ser | Gly | Tyr | Val | Ala | Ser | Gly | Glu | Glu | Val | |
| 70 | | | | | 75 | | | | | 80 | | | | | 85 | |
| ACA | GCT | GGT | AAA | CCT | GAT | TTC | CCT | GAA | ATC | TTC | ACT | GTC | TGC | AAG | GAC | 821 |
| Thr | Ala | Gly | Lys | Pro | Asp | Phe | Pro | Glu | Ile | Phe | Thr | Val | Cys | Lys | Asp | |
| | | | | 90 | | | | | 95 | | | | | 100 | | |
| TTG | TCG | GTA | GGC | GAT | CAG | CGT | GTA | AAA | GCC | GGC | TGG | CCT | TGC | CAT | GGT | 869 |
| Leu | Ser | Val | Gly | Asp | Gln | Arg | Val | Lys | Ala | Gly | Trp | Pro | Cys | His | Gly | |
| | | | | 105 | | | | | 110 | | | | | 115 | | |
| CCG | GTG | CCA | TGG | CCA | AAT | AAC | ACC | TAT | CAG | AAA | AGC | ATG | AAG | ACC | TTC | 917 |
| Pro | Val | Pro | Trp | Pro | Asn | Asn | Thr | Tyr | Gln | Lys | Ser | Met | Lys | Thr | Phe | |
| | | 120 | | | | | 125 | | | | | 130 | | | | |
| ATG | GAA | GAG | CTG | GGT | TTA | GCG | GGC | GAA | CGG | TTG | CTC | AAA | CTG | ACA | GCG | 965 |
| Met | Glu | Glu | Leu | Gly | Leu | Ala | Gly | Glu | Arg | Leu | Leu | Lys | Leu | Thr | Ala | |
| 135 | | | | | 140 | | | | | 145 | | | | | | |
| CTC | GGC | TTT | GAA | CTA | CCC | ATC | AAC | ACG | TTC | ACC | GAC | TTA | ACT | CGC | GAT | 1013 |
| Leu | Gly | Phe | Glu | Leu | Pro | Ile | Asn | Thr | Phe | Thr | Asp | Leu | Thr | Arg | Asp | |
| 150 | | | | | 155 | | | | | 160 | | | | | 165 | |
| GGT | TGG | CAC | CAC | ATG | CGT | GTA | TTA | CGC | TTC | CCG | CCC | CAA | ACA | TCC | ACG | 1061 |
| Gly | Trp | His | His | Met | Arg | Val | Leu | Arg | Phe | Pro | Pro | Gln | Thr | Ser | Thr | |
| | | | | 170 | | | | | 175 | | | | | 180 | | |
| CTG | TCC | CGT | GGA | ATT | GGT | GCG | CAC | ACT | GAT | TAT | GGG | TTG | TTG | GTA | ATT | 1109 |
| Leu | Ser | Arg | Gly | Ile | Gly | Ala | His | Thr | Asp | Tyr | Gly | Leu | Leu | Val | Ile | |
| | | | 185 | | | | | 190 | | | | | 195 | | | |
| GCC | GCT | CAG | GAC | GAT | GTT | GGT | GGC | TTA | TAT | ATT | CGC | CCT | CCA | GTC | GAG | 1157 |
| Ala | Ala | Gln | Asp | Asp | Val | Gly | Gly | Leu | Tyr | Ile | Arg | Pro | Pro | Val | Glu | |
| | | 200 | | | | | 205 | | | | | 210 | | | | |
| GGA | GAG | AAG | CGT | AAT | CGT | AAC | TGG | TTG | CCT | GGT | GAG | AGC | TCA | GCA | GGC | 1205 |
| Gly | Glu | Lys | Arg | Asn | Arg | Asn | Trp | Leu | Pro | Gly | Glu | Ser | Ser | Ala | Gly | |
| 215 | | | | | 220 | | | | | 225 | | | | | | |
| ATG | TTT | GAG | CAC | GAT | GAA | CCT | TGG | ACC | TTC | GTG | ACG | CCC | ACC | CCA | GGC | 1253 |
| Met | Phe | Glu | His | Asp | Glu | Pro | Trp | Thr | Phe | Val | Thr | Pro | Thr | Pro | Gly | |
| 230 | | | | | 235 | | | | | 240 | | | | | 245 | |
| GTG | TGG | ACA | GTT | TTC | CCA | GGT | GAT | ATC | TTG | CAG | TTC | ATG | ACC | GGC | GGC | 1301 |
| Val | Trp | Thr | Val | Phe | Pro | Gly | Asp | Ile | Leu | Gln | Phe | Met | Thr | Gly | Gly | |
| | | | | 250 | | | | | 255 | | | | | 260 | | |
| CAG | CTG | CTT | TCC | ACT | CCG | CAC | AAG | GTT | AAG | CTC | AAT | ACC | CGC | GAA | CGT | 1349 |
| Gln | Leu | Leu | Ser | Thr | Pro | His | Lys | Val | Lys | Leu | Asn | Thr | Arg | Glu | Arg | |
| | | | 265 | | | | | 270 | | | | | 275 | | | |
| TTC | GCC | TGC | GCT | TAT | TTT | CAT | GAG | CCT | AAT | TTT | GAA | GCA | TCC | GCC | TAT | 1397 |
| Phe | Ala | Cys | Ala | Tyr | Phe | His | Glu | Pro | Asn | Phe | Glu | Ala | Ser | Ala | Tyr | |
| | | 280 | | | | | 285 | | | | | 290 | | | | |
| CCG | TTG | TTC | GAG | CCC | AGC | GCC | AAT | GAG | CGT | ATT | CAT | TAT | GGT | GAG | CAC | 1445 |
| Pro | Leu | Phe | Glu | Pro | Ser | Ala | Asn | Glu | Arg | Ile | His | Tyr | Gly | Glu | His | |
| 295 | | | | | 300 | | | | | 305 | | | | | | |
| TTT | ACC | AAC | ATG | TTT | ATG | CGT | TGC | TAT | CCA | GAT | CGG | ATC | ACC | ACC | CAG | 1493 |
| Phe | Thr | Asn | Met | Phe | Met | Arg | Cys | Tyr | Pro | Asp | Arg | Ile | Thr | Thr | Gln | |
| 310 | | | | | 315 | | | | | 320 | | | | | 325 | |
| AGG | ATC | AAC | AAG | GAG | AAT | CGC | CTG | GCG | CAC | TTG | GAG | GAC | TTG | AAG | AAG | 1541 |
| Arg | Ile | Asn | Lys | Glu | Asn | Arg | Leu | Ala | His | Leu | Glu | Asp | Leu | Lys | Lys | |
| | | | | 330 | | | | | 335 | | | | | 340 | | |
| TAT | TCG | GAC | ACC | CGC | GCG | ACA | GGC | TCA | TGAGTCGACA | CCCTGCCCGG | | | | | | 1588 |
| Tyr | Ser | Asp | Thr | Arg | Ala | Thr | Gly | Ser | | | | | | | | |
| | | | 345 | | | | | 350 | | | | | | | | |

TGCTGCCGGA CAGGGGCCTT ATCGTTACTG GTGACTAATA ATTGGCATAT CAATGTCCAC 1648

TCAGCACCCA GATCTTATGA TCTGGGTGCT GAGTGGAGCA ATGTAACCAT TATGCTGAGC 1708

GTTCATGCAT AGGAATTTCA ATAATTCCTA TACAAGGCAA TCCGCCGAAA AAGGTCCCCT 1768

CGGCGTGATG CCAACGTGGC GTCGATGTCG GCAAAAAGCT T   1809

DNA FRAGMENT COMPRISING A GENE ENCODING ETHYLENE FORMING ENZYME OF BACTERIA AND THE USE THEREOF

TECHNICAL FIELD

This invention relates to a DNA fragment comprising a gene encoding an ethylene-forming enzyme of bacteria, a vector including the DNA fragment, transformants transformed with the vector, and a method for producing ethylene using the transformants.

BACKGROUND ART

While ethylene is produced from crude petroleum or natural gas, it has long been known that ethylene could also be formed by plants and microorganisms.

Chou et al. reported that α-ketoglutaric acid(α-KG) or L-glutamic acid(Glu) is a precursor of ethylene in *Penicillium digitatum*, a species of fungi (Arch. Biochem. Biophys., 157, 73, 1973), and Goto et al. reported that α-KG serves as a substrate in the ethylene forming system in cell-free extracts of *Pseudomonas syringae* which is one of the species of pathogenic bacteria for plants (Plant Cell Physiol., 28, 405, 1987).

Primrose et al. reported that, in the ethylene-forming system in cell-free extracts of *Escherichia coli*, 2-keto-4-methylthiobutyric acid(KMBA) which is a metabolic intermediate of L-methionine(Met) is a precursor of ethylene biosynthesis (J. Gen. Microbiol.,98,519, 1977). In all these reports, however, the true substrates and biosynthetic pathway of ethylene-forming reaction were not established because materials such as cultured cells of bacteria or their cell free extracts, which are supposed to contain a lot of impurities, were used in the experiments.

To make clear the pathway of the ethylene biosynthesis caused by the bacteria and the ethylene-forming enzyme reaction, the present inventors purified the enzyme catalyzing the ethylene formation to electrophoretically homogeneous state. The results revealed that the ethylene-forming reaction via KMBA is really radical reactions in which active oxygen is concerned (Fukuda et al., FEMS Microbiol. Lett., 60, 107, 1989). We have also investigated the ethylene-forming enzyme of *Penicillium digitatum* IFO 9372 via a α-KG and its enzymatic reaction (Fukuda et al., FEMS Microbiol.lett., 59, 1989), and the ethylene-forming enzyme of *Pseudomonas syringae* pv. phaseolicola PK2 via α-KG and its characteristics (Nagahama, Fukuda et al., J. Gen. Microbiol., 137, 2228, 1991).

Although the enzyme catalyzing the ethylene biosynthesis by bacteria was identified as well as the characteristics of the enzyme, by the present inventors as described above, the ability of ethylene formation in these ethylene-forming bacteria was not adequately sufficient.

For the purpose of fundamental breeding improvement of the ethylene-forming bacteria through a gene manipulation technique, *Pseudomonas syringae* pv. phaseolicola PK2 was selected for the object and its DNA sequence encoding the ethylene-forming enzyme was analyzed, thereby completing this invention.

DISCLOSURE OF INVENTION

To achieve the above described object, this invention is characterized in that a gene encoding an amino acid sequence represented by:

Sea ID No: 1 Met Thr Asn Leu Gln Thr Phe Glu Leu Pro Thr Glu Val Thr Gly Cys Ala Ala Asp Ile Ser Leu Gly Arg Ala Leu Ile Gln Ala Trp Gln Lys Asp Gly Ile Phe Gln Ile Lys Thr Asp Ser Glu Gln Asp Arg Lys Thr Gln Glu Ala Met Ala Ala Ser Lys Gln Phe Cys Lys Glu Pro Leu Thr Phe Lys Ser Ser Cys Val Ser Asp Leu Thr Tyr Ser Gly Tyr Val Ala Ser Gly Glu Glu Val Thr Ala Gly Lys Pro Asp Phe Pro Glu Ile Phe Thr Val Cys Lys Asp Leu Ser Val Gly Asp Gln Arg Val Lys Ala Gly Trp Pro Cys His Gly Pro Val Pro Trp Pro Asn Asn Thr Tyr Gln Lys Ser Met Lys Thr Phe Met Glu Glu Leu Gly Leu Ala Gly Glu Arg Leu Leu Lys Leu Thr Ala Leu Gly Phe Glu Leu Pro Ile Asn Thr Phe Thr Asp Leu Thr Arg Asp Gly Trp His His Met Arg Val Leu Arg Phe Pro Pro Gln Thr Ser Thr Leu Ser Arg Gly Ile Gly Ala His Thr Asp Tyr Gly Leu Leu Val Ile Ala Ala Gln Asp Asp Val Gly Gly Leu Tyr Ile Arg Pro Pro Val Glu Gly Glu Lys Arg Asn Arg Asn Trp Leu Pro Gly Glu Ser Ser Ala Gly Met Phe Glu His Asp Glu Pro Trp Thr Phe Val Thr Pro Tbr Pro Gly Val Trp Tbr Val Phe Pro Gly Asp Ile Leu Gln Phe Met Thr Gly Gly Gln Leu Leu Ser Thr Pro His Lys Val Lys Leu Asn Thr Arg Glu Arg Phe Ala Cys Ala Tyr Phe His Glu Pro Asn Phe Glu Ala Ser Ala Tyr Pro Leu Phe Glu Pro Ser Ala Asn Glu Arg Ile His Tyr Gly Glu His Phe Thr Asn Met Phe Met Arg Cys Tyr Pro Asp Arg Ile Thr Thr Gln Arg Ile Asn Lys Glu Asn Arg Leu Ala His Leu Glu Asp Leu Lys Lys Tyr Ser Asp Thr Arg Ala Thr Gly Ser is integrated into bacteria.

DNA encoding the ethylene-forming enzyme of the present invention can be obtained, for example, by the procedures comprising:

preparing a probe with an amino acid sequence coding the ethylene-forming enzyme from *Pseudomonas syringae*; hybridizing this probe with an indigenous plasmid by Southern method to find that a gene for the ethylene-forming enzyme is encoded in the indigenous plasmid DNA; constructing a gene library after transforming *Escherichia coli* (*E. coli*) using restriction enzyme Hind III fragments of this indigenous plasmid DNA and pUC19 as a vector; and screening a positive clone *E. coli* JM109 (pEFE01) from the library by a hybridization using Southern method.

Hind III fragments of about 2.5 kbp from *Pseudononas syringae* were inserted into the plasmid pUC19 in the cell of this positive clone *E. coli* JMO109(pEFE01), and an ethylene-forming activity was found in this positive clone *E. coli* JM109(pEFE01). This positive clone *E. coli* JM109(pEFE01) also expressed a protein that could not be distinguished from the ethylene-forming enzyme protein of *Pseudomonas syringae* as detected by Western blotting method using an antibody for the ethylene forming enzyme.

Deletion mutant strains having various sizes of plasmids were prepared by digesting the inserted 2.5kbp Hind III fragments. The smallest pEFEO1 derivative was obtained from the mutants keeping ethylene-forming activity. The size of the smallest fragment was about 1.5 kbp.

BRIEF DESCRIPTION OF DRAWOMGS

FIG. 1 shows a base sequence of the gene of the ethylene-forming enzyme after cloning and the first half portion of the amino acid sequence translated therefrom.

FIG. 1 shows a base sequence of the gene of the ethylene-forming enzyme after cloning and the latter half portion of the amino acid sequence translated therefrom.

BEST MODE FOR CARRYING OUT THE INVENTION

EXAMPLES

Chromosomal DNA of *Pseudomonas syringae* was extracted with phenol after lysis of cell wall with lysozyme and sodium dodecyl gulfate (SDS), wherein proteins were removed by denaturation and DNA was recovered from the supernatant by ethanol precipitation. The plasmid DNA of *Pseudomonas syringae* wae was extracted by an alkali extraction method.

Extracted DNA was digested with a restriction enzyme Hind III and the digested fragments were subjected to electrophoresis using 0.7% of agarose gel. DNA in the gel after the electrophoresis were transferred to a Nylon membrane by a capillary method, bound onto the membrane by a dry-heat treatment and were subjected to Southern hybridization.

Since the structural gene of the ethylene-forming enzyme (EFE) seemed to be located on the plasmid after the hybridization, the plasmid DNA fragments digested with Hind III are ligated with the *E. coli* vector (pUC19) subjected to an alkali phosphatase treatment, thereby obtaining the chimera plasmid. This chimera plasmid was mixed with competent cells of *Escherichia coli* (*E. coli* YM109) prepared by a calcium chloride method and, after allowing them to stand in an ice bath for an hour, the chimera plasmid was incorporated into the cell with a heat shock, followed by centrifugation, thereby transforming *E. coli* JM108. This *E. coli* JM109 after the transformation was seeded in 2xYT culture medium consisting of 16g/liter of Bactotrypton, 10g/liter of Bactoyeast extract and 5g/liter of sodium chloride. After the cultivation for 1.5 hours, *E. coii* JM109 was separated by centrifugation and inoculated in a selected culture medium.

Colonies having the chimera plasmid expressed in the selected culture medium were screened and these colonies were cultivated in LB culture medium consisting of 10g/liter of Bactotrypton, 5g/liter of Bactoyeast extract and 10g/liter of sodium chloride supplemented with 5 μg/ml of thiamine hydrochloride and 50 μg/ml of ampicillin sodium salt. The plasmid DNA (chimera pUC19) was extracted with an aqueous alkaline, purified by removing RNA and, after treating with Hind III, it was subjected to electrophoresis using 1% of agarose gel. The DNA after electrophoresis was denatured with an aqueous alkaline solution followed by neutralization and blotted on a nylon membrane, and then *E. coli* which retained the gene of the ethylene-forming enzyme was screened by hybridization.

When *E. coli* JM109(pEFE01) was cultivated in the above described LB culture medium supplemented with 5g/ml of L-glutamic acid, 5 μg/ml of thiamine hydrochloride and 50 μg/ml of ampicillin sodium salt, the ethylene-forming activity was 230nl/ml of culture medium/hr. In the above described *E. coli* JM109 (a disclosed strain well known in the art) used as a host, on the other hand, any ethylene-forming activity was not detected and its ethylene-forming rate was 0n1/ml of culture medium/hr. The term "ethylene-forming activity" used herein refers to an in vitro ethylene-forming ability in a cell-free extract prepared from the cells, and the term "ethylene-forming rate" refers to an in vivo ethylene-forming ability in the culture medium. These characteristics could be detected by conventional methods described, for example, in the above described reference (Nagahama, Fukuda et al., J. Gen. Microbiol., 37, 2281, 1991).

The transformant *Escherichia coli* JM109(pEFE01) used in this invention was deposited to National Institute of Bioscience and Human-Technology, 1–3, Higashi -chome, Tsukuba City, Japan, under the registration number of FERM P-1361 dated Sep. 16, 1992.

It was made clear by Western blotting that an identical protein with the ethylene-forming enzyme of *Pseudomonas syringae* was also present in *E. coli* JM109(pEFE01). Deletion mutant having various size of plasmids were prepared by digesting the inserted 2.5kbp Hind III fragment from its terminal. The smallest pEFE01 transformant retaining the ethylene-forming activity was about 1.5 kbp. In addition, neither site for Hind III nor sites for other restriction enzymes PstI, Dra I, EcoR I and BamH I were present in this fragment.

The base sequence and amino acid sequence of the gene of the ethylene forming-enzyme incorporated in 2.5 kbp Hind III fragment as determined by a dideoxy method are shown in FIG. 1 and FIG. 2.

Industrial Applicability

According to this invention, bacteria having high ethylene-forming activity can be obtained by transforming bacteria such as *E. coli* which is safe and easy in manipulation.

Moreover, ethylene can be produced with high efficiency by utilizing these transformed bacteria.

---

What is claimed is:

1. A DNA fragment comprising a gene encoding an ethylene-forming enzyme of bacteria represented by the following amino acid sequence:

SEQ ID NO:1:
Met Thr Asn Leu Gln Thr Phe Glu Leu Pro Thr Glu Val
Thr Gly Cys Ala Ala Asp Ile Ser Leu Gly Arg Ala
Leu Ile Gln Ala Trp Gln Lys Asp Gly Ile Phe Gln Ile
Lys Thr Asp Ser Glu Gln Asp Arg Lys Thr Gln Glu
Ala Met Ala Ala Ser Lys Gln Phe Cys Lys Glu Pro
Leu Thr Phe Lys Ser Ser Cys Val Ser Asp Leu Thr
Tyr Ser Gly Tyr Val Ala Ser Gly Glu Glu Val Thr Ala
Gly Lys Pro Asp Phe Pro Glu Ile Phe Thr Val Cys Lys
Asp Leu Ser Val Gly Asp Gln Arg Val Lys Ala Gly
Trp Pro Cys His Gly Pro Val Pro Trp Pro Asn Asn
Thr Tyr Gln Lys Ser Met Lys Thr Phe Met Glu Glu
Leu Gly Leu Ala Gly Glu Arg Leu Leu Lys Leu Thr
Ala Leu Gly Phe Glu Leu Pro Ile Asn Thr Phe Thr
Asp Leu Thr Arg Asp Gly Trp His His Met Arg Val
Leu Arg Phe Pro Pro Gln Thr Ser Thr Leu Ser Arg
Gly Ile Gly Ala His Thr Asp Tyr Gly Leu Leu Val Ile
Ala Ala Gln Asp Asp Val Gly Gly Leu Tyr Ile Arg Pro
Pro Val Glu Gly Glu Lys Arg Asn Arg Asn Trp Leu
Pro Gly Glu Ser Ala Gly Met Phe Glu Leu His Asp
Glu Pro Trp Thr Phe Val Thr Pro Thr Pro Gly Val Trp
Thr Val Phe Pro Gly Asp Ile Leu Gln Phe Met Thr
Gly Gly Gln Leu Leu Ser Thr Pro His Lys Val Lys
Leu Asn Thr Arg Glu Arg Phe Ala Cys Ala Tyr Phe
His Glu Pro Asn Phe Glu Ala Ser Ala Tyr Pro Leu
Phe Glu Pro Ser Ala Asn Glu Arg Ile His Tyr Gly Glu
His Phe Thr Asn Met Phe Met Arg Cys Tyr Pro Asp
Arg Ile Thr Thr Gln Arg Ile Asn Lys Glu Asn Arg Leu
Ala His Leu Glu Asp Leu Lys Lys Tyr Ser Asp Thr
Arg Ala Thr Gly Ser

2. A DNA fragment according to claim 1 which comprises a gene encoding an ethylene-forming enzyme of bacteria, wherein said bacteria belong to a genus Pseudomonas.

3. A DNA fragment according to claim 1 which comprises a gene encoding an ethylene-forming enzyme of bacteria represented by the following base sequence:

SEQ ID NO:2
ATG ACC AAC CTA CAG ACT TTC GAG TTG CCT
ACC GAG GTA ACC GGC TGC GCC GCC GAT
ATC TCA TTG GGA AGG GCG CTG ATC CAA
GCC TGG CAA AAA GAT GGC ATT TTT CAG
ATC AAG ACC GAT AGT GAG CAG GAT CGC
AAA ACG CAG GAA GCA ATG GCT GCT AGC
AAG CAG TTT TGC AAG GAA CCG CTG ACT
TTT AAG AGT AGC TGC GTT AGC GAT CTG
ACC TAC AGC GGC TAT GTT GCG TCA GGC
GAG GAA GTC ACA GCT GGT AAA CCT GAT
TTC CCT GAA ATC TTC ACT GTC TGC AAG
GAC TTG TCG GTA GGC GAT CAG CGT GTA
AAA GCC GGC TGG CCT TGC CAT GGT CCG
GTG CCA TGG CCA AAT AAC ACC TAT CAG
AAA AGC ATG AAG ACC TTC ATG GAA GAG
CTG GGT TTA GCG GGC GAA CGG TTG CTC
AAA CTG ACA GCG CTC GGC TTT GAA CTA
CCC ATC AAC ACG TTC ACC GAC TTA ACT
CGC GAT GGT TGG CAC CAC ATG CGT GTA
TTA CGC TTC CCG CCC CAA ACA TCC ACG
CTG TCC CGT GGA ATT GGT GCG CAC ACT
GAC TAT GGG TTG TTG GTA ATT GCC GCT
CAG GAC GAT GTT GGT GGC TTA TAT ATT
CGC CCT CCA GTC GAG GGA GAG AAG CGT
AAT CGT AAC TGG TTG CCT GGT GAG AGC
TCA GCA GGC ATG TTT GAG CAC GAT GAA
CCT TGG ACC TTC GTG ACG CCC ACC CCA
GGC GTG TGG ACA GTT TTC CCA GGT GAT
ATC TTG CAG TTC ATG ACC GGC GGC CAG
CTG CTT TCC ACT CCG CAC AAG GTT AAG
CTC AAT ACC CGC GAA CGT TTC GCC TGC
GCT TAT TTT CAT GAG CCT AAT TTT GAA
GCA TCC GCC TAT CCG TTG TTC GAG CCC
AGC GCC AAT GAG CGT ATT CAT TAT GGT
GAG CAC TTT ACC AAC ATG TTT ATG CGT
TGC TAT CCA GAT CGG ATC ACC ACC CAG
AGG ATC AAC AAG GAG AAT CGC CTG GCG
CAC TTG GAG GAC TTG AAG AAG TAT TCG
GAC ACC CGC GCG ACA GGC TCA

4. A DNA fragment according to claim 1 which comprises a gene encoding an ethylene-forming enzyme of bacteria, wherein said fragment has a base sequence of at least from No. 519 to No. 1568 of the following base sequence:

SEQ ID NO:3:

```
        10         20         30         40         50
GCGACCGCGTGTCAGCAACGACAATCCTTACTCGGAGTCGCTGTTCAGGACACTGAAGT 60         70         80         90        100        110
ACTGCCCGCAATGGCCGCAGGATGGGTTTGCCAGTCTTGACGCGGCACGCTCTGGGTGAG 120        130        140        150        160        170
GGATTTCATGCGTTGGTACAACAATGATCACCGGCACAGCCGAATCCGCTTCGTGACACC 180        190        200        210        220        230
GGCTGAGCGGCATCGAGGGCTGGATCATCAGATCCTGGCCAAGCGACATGAGCTGTACGA 240        250        260        270        280        290
GCTAGCCAGAGAGAAAAGGCCGGAGCGGTGGTCGAGGGAGACACGCAACTGGGAACCGAT 300        310        320        330        340        350
CGGCACCGTGCTGTTAAACCCGGATCGAGAGCAAGACGTTGAGAAAAAAGCAGCATAGTT 360        370        380        390        400        410
AGACGGTTGACGCGACAACTACCTTGAAAAACGCCGGCAGGGACGCTCATGATTCATGCT
```

-continued

```
     420       430       440       450       460       470
CCAAGCAGGTGGGGTGTTTTTCCGTCGCTTGGACTTTGTTCTCCCGACGTCGTTTGGAAT 480       490       500       510       520       530
GAGCATCCGTCCCTTTATATGGATAAAGAAGAGACTAGCATGACCAACCTACAGACTTTC 540       550       560       570       580       590
GAGTTGCCTACCGAGGTAACCGGCTGCGCCGCCGATATCTCATTGGGAAGGGCGCTGATC 600       610       620       630       640       650
CAAGCCTGGCAAAAAGATGGCATTTTTCAGATCAAGACCGATAGTGAGCAGGATCGCAAA 660       670       680       690       700       710
ACGCAGGAAGCAATGGCTGCTAGCAAGCAGTTTTGCAAGGAACCGCTGACTTTTAAGAGT 720       730       740       750       760       770
AGCTGCGTTAGCGATCTGACCTACAGCGGCTATGTTGCGTCAGGCGAGGAAGTCACAGCT 780       790       800       810       820       830
GGTAAACCTGATTTCCCTGAAATCTTCACTGTCTGCAAGGACTTGTCGGTAGGCGATCAG 840       850       860       870       880       890
CGTGTAAAAGCCGGCTGGCCTTGCCGTGGTCCGGTGCCATGGCCAAATAACACCTATCAG 900       910       920       930       940       950
AAAAGCATGAAGACCTTCATGGAAGAGCTGGGTTTAGCGGGCGAACGGTTGCTCAAACTG 960       970       980       990      1000      1010
ACAGCGCTCGGCTTTGAACTACCCATCAACACGTTCACCGACTTAACTCGCGATGGTTGG 1020      1030      1040      1050      1060      1070
CACCACATGCGTGTATTACGCTTCCCGCCCCAAACATCCACGCTGTCCCGTGGAATTGGT 1080      1090      1100      1110      1120      1130
GCGCACACTGACTATGGGTTGTTGGTAATTGCCGCTCAGGACGATGTTGGTGGCTTATAT 1140      1150      1160      1170      1180      1190
ATTCGCCCTCCAGTCGAGGGAGAGAAGCGTAATCGTAACTGGTTGCCTGGTGAGAGCTCA 1200      1210      1220      1230      1240      1250
GCAGGCATGTTTGAGCACGATGAACCTTGGACCTTCGTGACGCCCACCCCAGGCGTGTGG 1260      1270      1280      1290      1300      1310
ACAGTTTTCCCAGGTGATATCTTGCAGTTCATGACCGGCGGCCAGCTGCTTTCCACTCCG 1320      1330      1340      1350      1360      1370
CACAAGGTTAAGCTCAATACCCGCGAACGTTTCGCCTGCGCTTATTTTCATGAGCCTAAT 1380      1390      1400      1410      1420      1430
TTTGAAGCATCCGCCTATCCGTTGTTCGAGCCCAGCGCCAATGAGCGTATTCATTATGGT 1440      1450      1460      1470      1480      1490
GAGCACTTTACCAACATGTTTATGCGTTGCTATCCAGATCGGATCACCACCCAGAGGATC 1500      1510      1520      1530      1540      1550
AACAAGGAGAATCGCCTGGCGCACTTGGAGGACTTGAAGAAGTATTCGGACACCCGCGCG 1560      1570      1580      1590      1600      1610
ACAGGCTCATGAGTCGACACCCTGCCCGGTGCTGCCGGACAGGGGCCTTATCGTTACTGG 1620      1630      1640      1650      1660      1670
TGACTAATAATTGGCATATCAATGTCCACTCAGCACCCAGATCTTATGATCTGGGTGCTG 1680      1690      1700      1710      1720      1730
AGTGGAGCAATGTAACCATTATGCTGAGCGTTCATGCATAGGAATTTCAATAATTCCTAT 1740      1750      1760      1770      1780      1790
ACAAGGCAATCCGCCGAAAAAGGTCCCCTCGGCGTGATGCCAACGTGGCGTCGATGTCGG

1800
CAAAAAGCTT
```

5. A vector which includes a DNA fragment which encodes the amino acid sequence defined in SEQ ID NO:1.

6. A host cell which has been transformed by the vector of claim 5.

7. The host cell of claim 6 wherein said host cell is *E. coli*.

* * * * *